June 4, 1974 R. S. MOORE Plant Pat. 3,562
ROSE PLANT
Filed Jan. 10, 1973
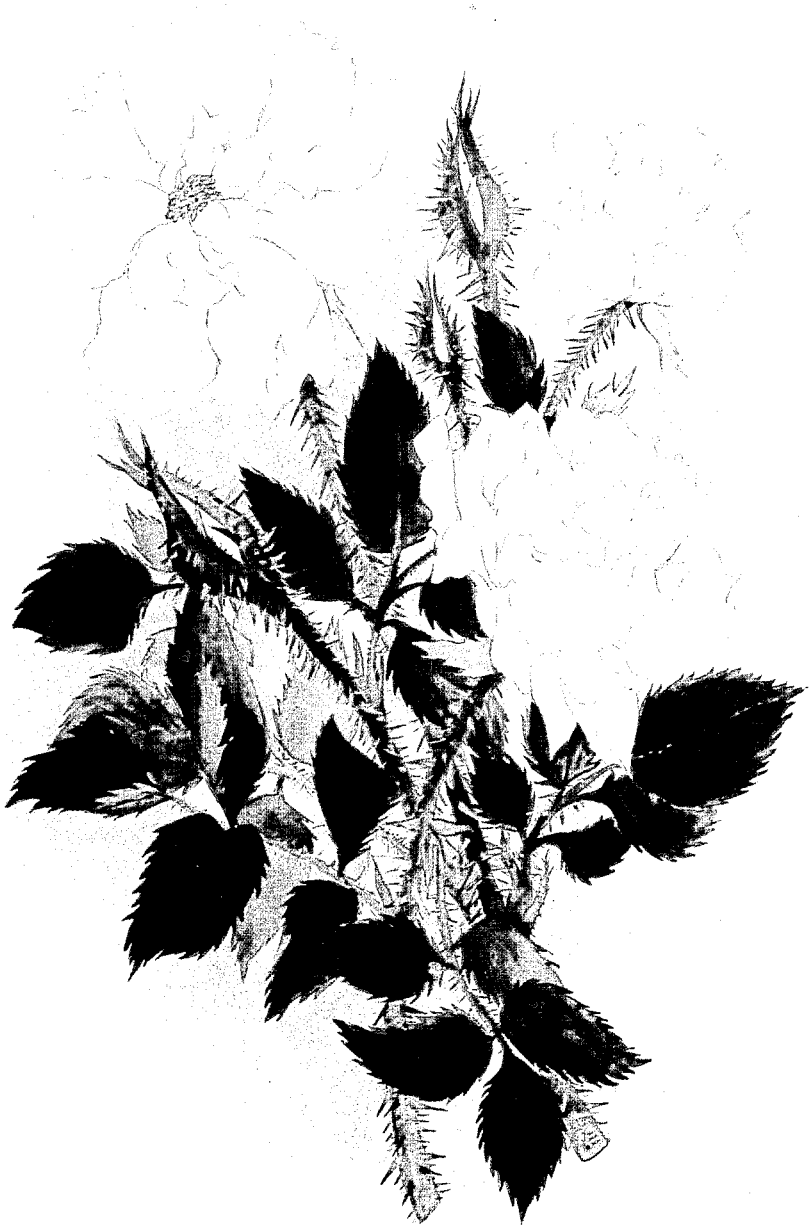

United States Patent Office

Plant Pat. 3,562
Patented June 4, 1974

3,562
ROSE PLANT

Ralph S. Moore, 2519 E. Noble Ave.,
Visalia, Calif. 93277

Filed Jan. 16, 1973, Ser. No. 324,177
Int. Cl. A01h 5/00
U.S. Cl. Plt.—24 1 Claim The present invention relates to a new and distinct variety of hardy, dwarf, bush type rose plant of the hybrid moss class, the variety being primarily characterized—as to novelty—by the pointed buds which on the basal portion are covered with numerous slender, relatively soft, thorns and on the upper portion (sepals) covered with relatively soft "moss."

The variety is further characterized by:

Clear yellow buds and flowers similar to Greenfire P.P. #1,776 in general color effect, unusual for roses of the moss class.

An abundance of bloom, with flowers on mature plants borne singly and in loose clusters of three or more to the stem.

A plant which is vigorous, of upright habit, with glossy, medium green leaves. A plant, which has a normal average height of about 3 feet at maturity, resembling the general plant habit of Rumba (Plant Pat. #1,919), a greenhouse floribunda variety.

A plant which grows and blooms satisfactorily in the greenhouse or in the garden; and provides long lasting cut flowers.

The present variety of moss rose was originated by me in my nursery located at Visalia, Calif., under conditions of careful control and observation, as a cross of Rumba (U.S. Plant Pat. #1,776) as the seed parent × an unnamed yellow moss rose hybrid as the pollen parent.

Subsequent to origination of the variety I successfully asexually reproduced it, in my nursery located as aforesaid, by budding as well as by cuttings; the reproductions having run true in all respects.

The Figure of the drawing illustrates a spray, including foliage, buds and flowers.

Referring now specifically to the new and distinct variety of moss rose plant, the following is a detailed description thereof in outline: all major color identifications being by reference to the British Colour Council Colour Chart, except where common terms of color definition are employed.

Type: Hardy; medium dwarf; bush; seedling; outdoors; greenhouse; garden decoration; cut flowers.

Class: Floribunda Moss.

Flowers: Continuity—continuous repeat bloom during growing season. Fragrance—very fragrant.

Flowers borne: Sometimes singly on young plants usually several together (3–5) in loose cluster, on medium length sturdy stem, on mature plants.

Quantity of bloom: Average abundance.

Bud: Peduncle—medium length; sturdy; erect; medium green.

*Before calyx breaks.*—Size—medium. Form: long pointed with lower portion of bud covered with numerous slender relatively soft thorns, foliaceous appendages and moss-like structures on sepals; with foliaceous parts extending beyond the tip of the bud equal to one-half or more of its length.

*Color.*—Medium green.

*As calyx breaks.*—Color—greenish yellow. As first petal opens: yellow. Size: medium.

*Form.*—Long pointed. Color—outside: Straw Yellow 604 shading deeper toward the base. Inside: Empire Yellow 603 shading deeper toward the base.

*Open.*—Opens well in all weather.

Bloom:

*Size when fully open.*—Medium—about 3".

*Petalage.*—Double—varies with the season but averages 20–25.

*Form.*—High center at first, becoming open in center.

Petals: Firm: satiny on both upper and lower surface.

*Shape.*—Outside petals broad lanceolate (wedge shaped), tip round; intermediate—broad lanceolate (wedge shape) with nearly round tip; inside—lanceolate (usually with rounded tip).

Color: Newly opened flower from plant grown in plastic house (November 1972), Visalia, Calif.:

*Outside petal.*—Outside surface—Straw Yellow 604 with darker and lighter tones. Inside surface: Empire Yellow 603 shading into deeper yellow near base.

*Intermediate petal.*—Outside surface—Straw Yellow 604 with darker tones. Inside surface—Empire Yellow 603 and shading into deeper yellow at base.

*Inner petal.*—Outside surface—Straw Yellow 604 to Chinese Yellow 606. Inside surface—similar to intermediate petal.

*General color effect.*—Newly opened flower—clear bright yellow. Three days open—lighter yellow. Behaviour—often changes to near white and pink as flower ages, hangs on for a time, then drops. Flower longevity (September-October 1972), bush in garden 5–7 days or longer. Cut flowers kept at living room temperature—4–7 days.

Reproductive organs:

*Stamens.*—Numerous; arranged regularly about pistil.

*Filments.*—Medium length.

*Antheres.*—Numerous, well formed.

*Pollen.*—Moderately abundant, yellow.

*Pistals.*—Moderate number.

*Styles.*—Uneven, relatively long, bunched.

*Stigma.*—Usually well formed and functional.

*Ovaries.*—All enclosed in calyx.

*Hips.*—Few, covered with thorns, orange.

*Sepals.*—Permanent; spear shaped; covered with moss on outside surface.

*Seeds.*—Few.

Foliage:

*Leaves.*—Compound of 5, sometimes 3, leaflets; abundant, medium, leathery, glossy.

*Leaflets.*—Shape: lanceolate; apex acute, base round.

*Margin.*—Serrate. Color: medium green; new leaves sometimes tinted reddish.

*Rachis.*—Strong; upper surface grooved with numerous very short hairs; under side moderately thorny.

*Stipules.*—Medium to long; medium width; medium length points, turning out at an angle of about 45 degrees.

Growth: Habit—compact; bushy; upright; much branched.

*Growth.*—Vigorous. Canes—medium to strong, Main stems—color: dark green to brownish. Thorns: thorny; long oval base; medium length; straight or hooked slightly downward. Color—brown. Prickles: numerous.

*Branches.*—Color: medium green to brownish. Thorns: quite thorny; medium length; hooked slightly downward; long oval base; color—reddish to brown.

*New shoots.*—Color: medium to bright green, sometimes lightly tinted reddish; Thorns: quite thorny; medium to long, slender; hooked slightly downward; long oval base. Color: reddish. Prickles: numerous. Hairs: some.

The following is claimed:

1. A new and distinct variety of moss rose plant of hardy, moderately dwarf, upright, much branched, bush type, as illustrated and described, characterized by buds and flowers resembling Greenfire (U.S. Plant Pat. #1,776) floribunda rose in color and general color effect; further characterized by flower buds having numerous, relatively soft, green thorns covering basal portion with abundant moss-like appendages covering sepals; and further characterized by a plant which is vigorous in growth, easy to propagate from cuttings and by budding, with abundant medium size, medium green, glossy foliage, an abundance of bloom, recurring repeatedly throughout the growing season with flowers borne singly and in loose cluster of 3 to 5.

No references cited.

ROBERT E. BAGWILL, Primary Examiner